(12) United States Patent
McGhie

(10) Patent No.: US 10,448,930 B2
(45) Date of Patent: Oct. 22, 2019

(54) METHODS AND DEVICES FOR MAXIMIZING TISSUE COLLECTION IN PARTIAL-CORE BIOPSY NEEDLES

(75) Inventor: Thomas W. McGhie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 332 days.

(21) Appl. No.: 13/450,910

(22) Filed: Apr. 19, 2012

(65) Prior Publication Data

US 2013/0102925 A1   Apr. 25, 2013

Related U.S. Application Data

(60) Provisional application No. 61/482,491, filed on May 4, 2011.

(51) Int. Cl.
*A61B 10/02* (2006.01)
*A61B 17/32* (2006.01)

(52) U.S. Cl.
CPC ...... *A61B 10/0233* (2013.01); *A61B 10/0275* (2013.01); *A61B 2017/320064* (2013.01)

(58) Field of Classification Search
CPC .... A61B 10/0275; A61B 2017/320064; A61B 10/0233
USPC .......................................................... 600/567
See application file for complete search history.

(56) References Cited

U.S. PATENT DOCUMENTS

| | | |
|---|---|---|
| 4,055,167 A | 10/1977 | Bernstein |
| 4,627,444 A | 12/1986 | Brooker |
| 4,702,260 A | 10/1987 | Wang |
| 4,791,937 A | 12/1988 | Wang |
| 4,900,300 A | 2/1990 | Lee |
| 4,903,709 A | 2/1990 | Skinner |
| 4,989,614 A | 2/1991 | Dejter, Jr. et al. |
| 4,991,592 A | 2/1991 | Christ |
| 5,106,364 A | 4/1992 | Hayafuji et al. |
| 5,320,110 A * | 6/1994 | Wang ................. A61B 10/0275 600/566 |
| 5,449,001 A * | 9/1995 | Terwilliger ........ A61B 10/0275 600/567 |
| 5,458,112 A | 10/1995 | Weaver |
| 5,470,308 A | 11/1995 | Edwards et al. |
| 5,807,304 A | 9/1998 | Cockburn |
| 5,817,033 A | 10/1998 | DeSantis et al. |
| 5,865,765 A | 2/1999 | Mohajer |
| 5,971,939 A | 10/1999 | DeSantis et al. |
| 5,989,196 A * | 11/1999 | Chu ................... A61B 10/0275 600/567 |

(Continued)

FOREIGN PATENT DOCUMENTS

CN   2449657 Y   9/2001

OTHER PUBLICATIONS

Chhieng, David C. et al., "Fine-Needle Aspiration Cytology of Hodgkin Disease," Cancer Cytopathology, 2001, American Cancer Society, pp. 52-59.

(Continued)

*Primary Examiner* — Patrick Fernandes
(74) *Attorney, Agent, or Firm* — Brinks Gilson & Lione

(57) ABSTRACT

Methods and devices are illustrated for improving a partial-core biopsy device whereby inner mandrel deflection and flexibility is reduced, the volume of space available for tissue collection is increased, and tissue migration is reduced.

19 Claims, 4 Drawing Sheets

(56) References Cited

U.S. PATENT DOCUMENTS

| | | | |
|---|---|---|---|
| 6,193,673 B1 * | 2/2001 | Viola | A61B 10/0275 600/568 |
| 6,709,408 B2 | 3/2004 | Fisher | |
| 2009/0118641 A1 | 5/2009 | Van Dam et al. | |

OTHER PUBLICATIONS

Davenport, R.D., "Rapid on-site evaluation of transbronchial aspirates," Chest, 1990, vol. 98, pp. 59-61.

Diette, Gregory B., "Utility of On-Site Cytopathology Assessment for Bronchoscopic Evaluation of Lung Masses and Adenopathy," Chest, 2000, vol. 117, pp. 1186-1190.

Gittlen, S.D., "A new versatile transbronchial cytology needle for the staging and diagnosis of bronchogenic carcinoma," Chest, 1988, vol. 94, pp. 561-565.

Kaffes, Arthur J., "Fine Needle Aspiration at Endoscopic Ultrasound With a Novel Olympus Side-Port Needle: A Pilot Experience," Gastrointestinal Endoscopy, Abstract T1492, 2010, vol. 71, No. 5, p. 291.

Mayall, Frederick et al., "Improved FNA cytology results with a near patient diagnosis service for non-breast lesions," J. Clin. Pathol., 1998, vol. 51, pp. 541-544.

Mazzone MD, Peter et al., "Bronchoscopy and Needle Biopsy Techniques for Diagnosis and Staging of Lung Cancer," Clinics in Chest Medicine, vol. 23, No. 1, Mar. 2002, pp. 137.

McLoud MD, Theresa C., "Should Cutting Needles Replace Needle Aspiration of Lung Lesions?", Radiology, Jun. 1998, pp. 569-570.

Olympus KeyMed, Diagnosis (Needle Aspiration), keymed.co.uk/index.cfm/page/.../615, 2010, 2 pages.

Olympus EndoTherpay, SmoothShot, Expanded Line of Transbronchial Aspiration Needles Provides Comprehensive Scope Compatibility, Exceptional Puncture Performance, and Improved Operability, date unknown, 3 pages.

Shure, D., "Transbronchial biopsy and needle aspiration," Chest, 1989, vol. 95, pp. 1130-1138.

Trumm, C.G. et al., "Biopsy," Ch. 9, date unknown, pp. 94-95.

Wang, K.P., "Flexible transbronchial needle aspiration biopsy for histologic specimens," Chest, 1985, vol. 88, pp. 860-863.

Wang, Ko Pen, "Biopsy Sampling Technique," Chest, 1989, vol. 95, pp. 484-485.

Wang, K.P. et al., "Needle brush in the diagnosis of lung mass or nodule through flexible bronchoscopy," Chest, 1991, vol. 100, pp. 1148-1150.

Weisbrod, Gordon L. et al., "Preliminary Experience with a Dual Cutting Edge Needle in Thoracic Percutaneous Fine-Needle Aspiration Biopsy," Radiology, Apr. 1987, pp. 75-78.

Yang, Grace, C.H. et al., "Ultrasound-Guided Fine-Needle Aspiration of the Thyroid Assessed by Ultrafast Papanicoiaou Stain: Data from 1135 Biopsies with a Two to Six Year Follow-Up," Thyroid, vol. 11, No. 6, 2001, pp. 581-589.

Mazzone MD, Peter et al., "Bronchoscopy and Needle Biopsy Techniques for Diagnosis and Staging of Lung Cancer," Clinics in Chest Medicine, vol. 23, No. 1, Mar. 2002, pp. 137-158.

Yang, Grace, C.H. et al., "Ultrasound-Guided Fine-Needle Aspiration of the Thyroid Assessed by Ultrafast Papanicolaou Stain: Data from 1135 Biopsies with a Two to Six Year Follow-Up," Thyroid, vol. 11, No. 6, 2001, pp. 581-589.

\* cited by examiner

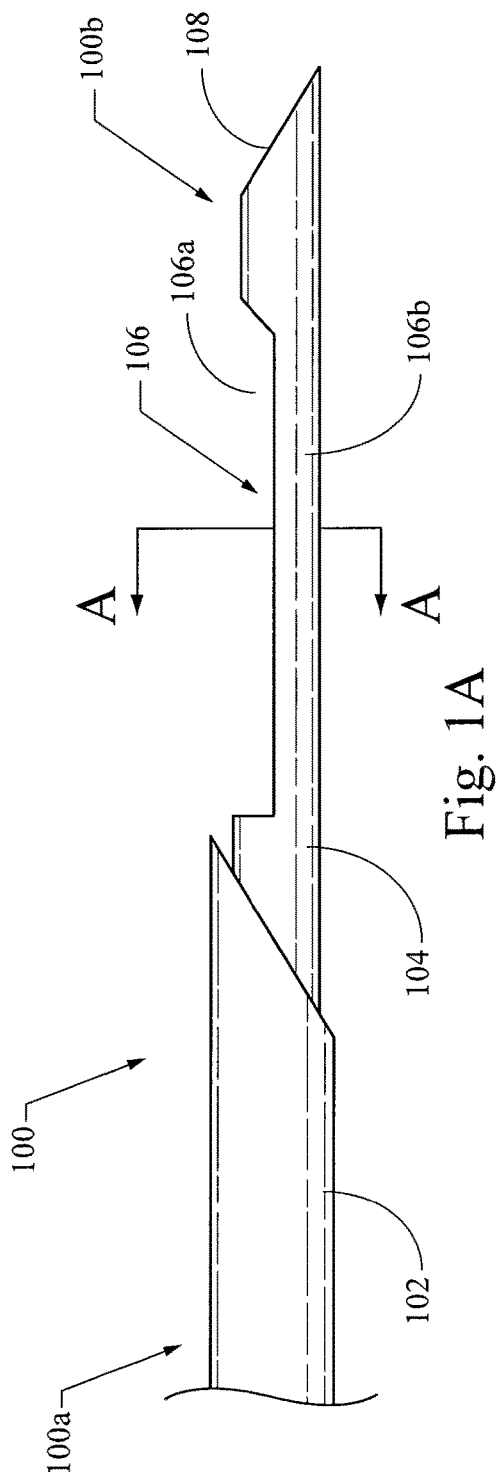
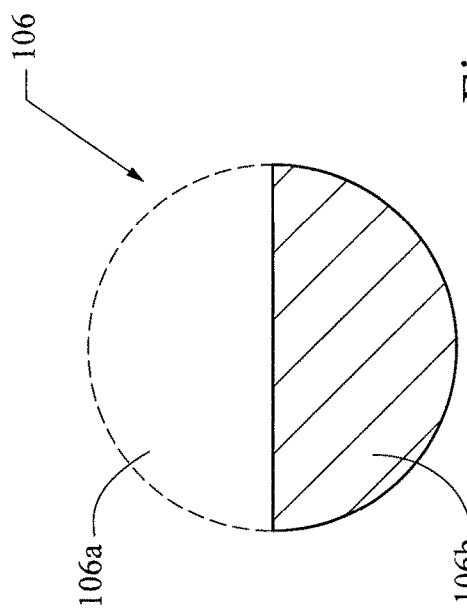

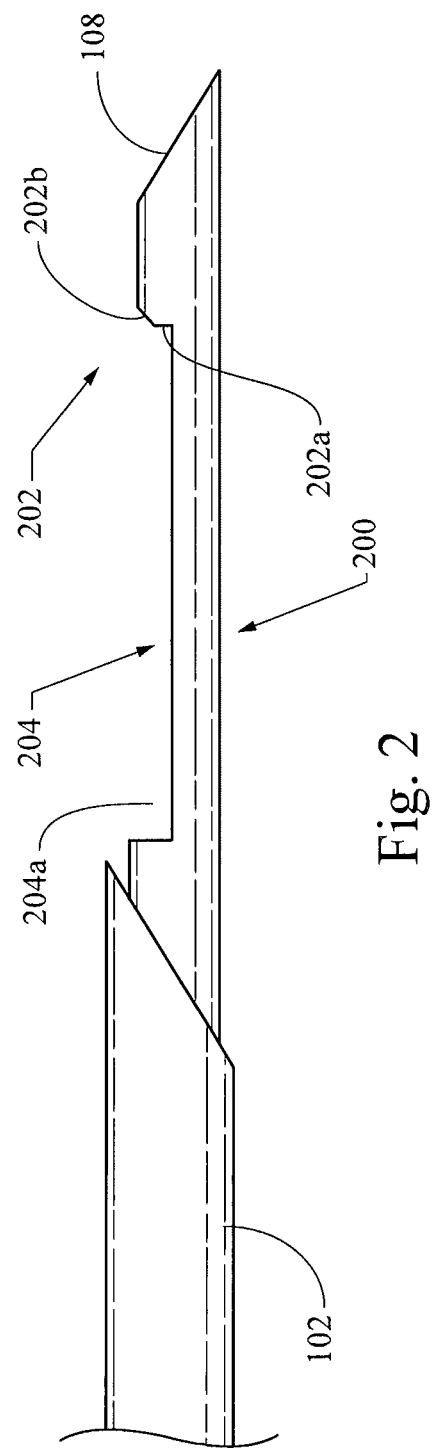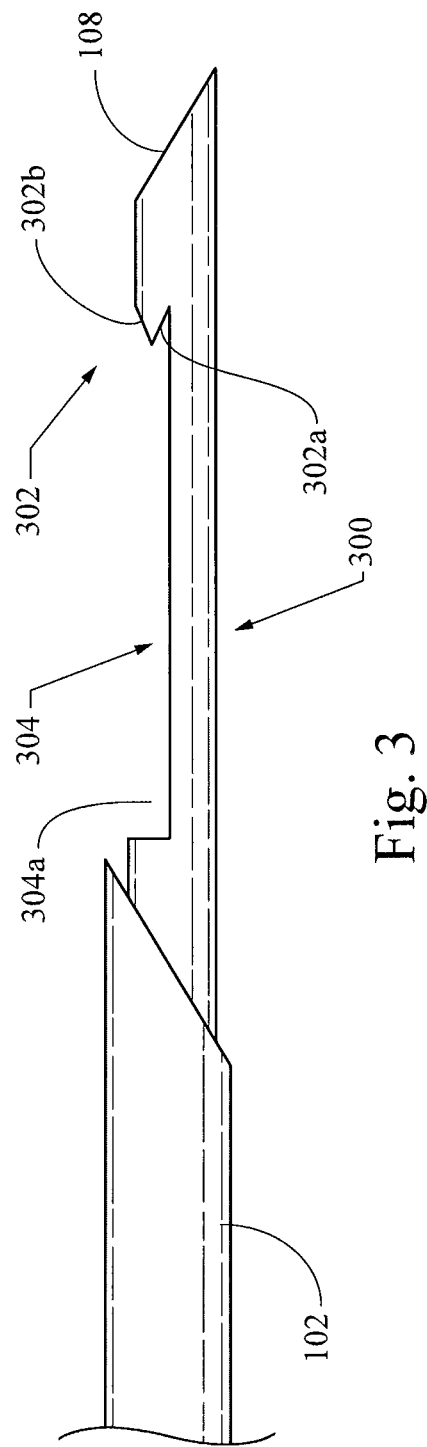

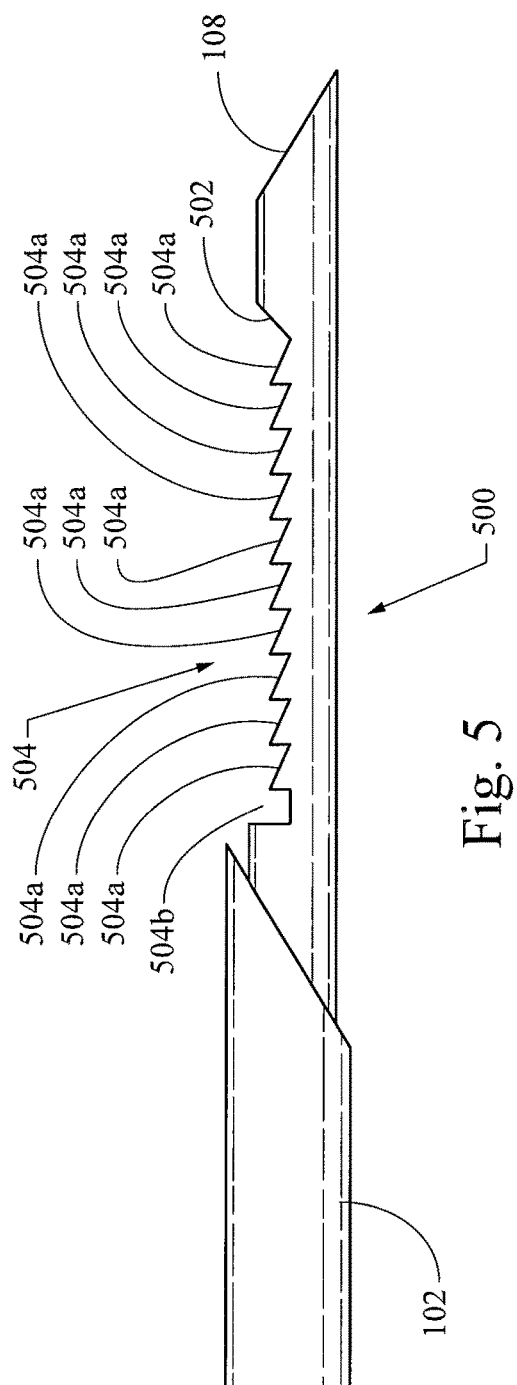
Fig. 5
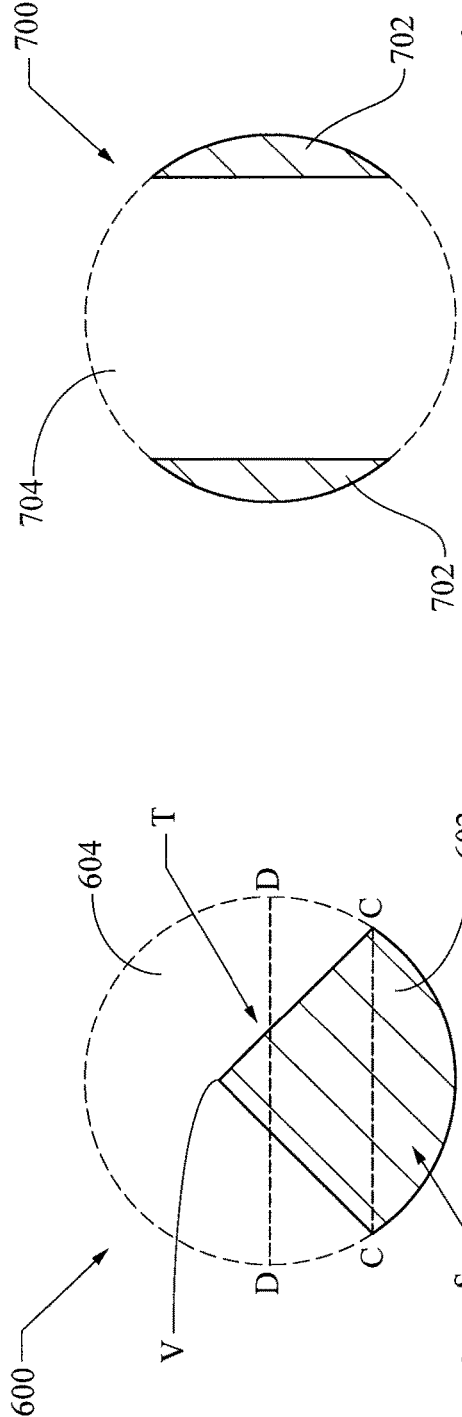
Fig. 7
Fig. 6

METHODS AND DEVICES FOR MAXIMIZING TISSUE COLLECTION IN PARTIAL-CORE BIOPSY NEEDLES

RELATED APPLICATION

This application claims the benefit of priority from U.S. Provisional Application No. 61/482,491, filed May 4, 2011, and titled "Methods and Devices for Maximizing Tissue Collection in Partial-Core Biopsy Needles", the contents of which is incorporated herein by reference.

TECHNICAL FIELD

The present invention relates to medical devices and more specifically, partial-core biopsy needle devices.

BACKGROUND

Biopsies are important medical tests used to collect cells or tissue for examination so as to determine the presence, extent, or likelihood of disease, trauma, ailment, or for other diagnostic or therapeutic applications. Current partial-core biopsy needle devices used to collect biopsy samples suffer from many shortcomings such as tissue migrating from the device before being collected, the limited amount of tissue the device is able to capture per procedure or "stick," and the deflection of the device resulting in the targeted tissue not being captured, trauma to the targeted tissue or surrounding area, and a reduced volume of collected material.

BRIEF SUMMARY

In a first aspect, a biopsy device is provided having a first elongated tubular body having a proximal portion and a distal portion; a second elongated tubular body having a proximal portion and a distal portion; and a notch disposed into the distal portion of the first elongated tubular body, wherein the notch includes: a void configured for partially encapsulating a tissue; a surface disposed in communication with the void, wherein the surface defines a boundary of at least a portion of the void and wherein the surface includes a longitudinal axis generally parallel to the first elongated tubular body; a tissue stop in communication with a distal portion of the void and configured for preventing tissue migration; and a shoulder in communication with the tissue stop disposed at an angle different from the surface and configured for deflecting the second elongated tubular body when directed distally over the notch.

In a second aspect, a biopsy device is provided having an elongated tubular body having a proximal portion and a distal portion; and a notch disposed into the distal portion of the elongated tubular body, wherein the notch includes: a void configured for partially encapsulating a tissue; and a surface disposed in communication with the void, wherein the surface defines a boundary of at least a portion of the void, wherein the surface and void are configured to reduce the flexibility of the elongated tubular body.

In a third aspect, a partial-core biopsy device is provided having an elongated tubular body having a proximal portion, a distal portion, and a generally circular cross-sectional area having four equally sized and shaped quadrants; and a notch disposed into the distal portion of the elongated tubular body, wherein the notch is bounded by a surface, wherein the notch includes a means for reducing tissue migration, and wherein the surface of the notch is less than one-half the total cross-sectional area of the elongated tubular body and is disposed into each of the four quadrants.

BRIEF DESCRIPTION OF THE SEVERAL VIEWS OF THE DRAWINGS

The embodiments will be further described in connection with the attached drawing figures. It is intended that the drawings included as a part of this specification be illustrative of the exemplary embodiments and should in no way be considered as a limitation on the scope of the invention. Indeed, the present disclosure specifically contemplates other embodiments not illustrated but intended to be included in the claims.

FIG. 1A is a side view of a typical partial-core biopsy needle;

FIG. 1B is a cross-sectional view of a typical inner mandrel along the line A-A shown in FIG. 1A;

FIG. 2 illustrates a side view of an exemplary improved inner mandrel;

FIG. 3 illustrates a side view of an alternate exemplary improved inner mandrel;

FIG. 5 illustrates a side view of an alternate exemplary improved inner mandrel;

FIG. 6 illustrates a cross-sectional view of an exemplary improved notch of an exemplary inner mandrel; and FIG. 7 illustrates a cross-sectional view of an alternate exemplary improved notch of an exemplary inner mandrel.

DETAILED DESCRIPTION OF PRESENTLY PREFERRED EMBODIMENTS

Figure 4:
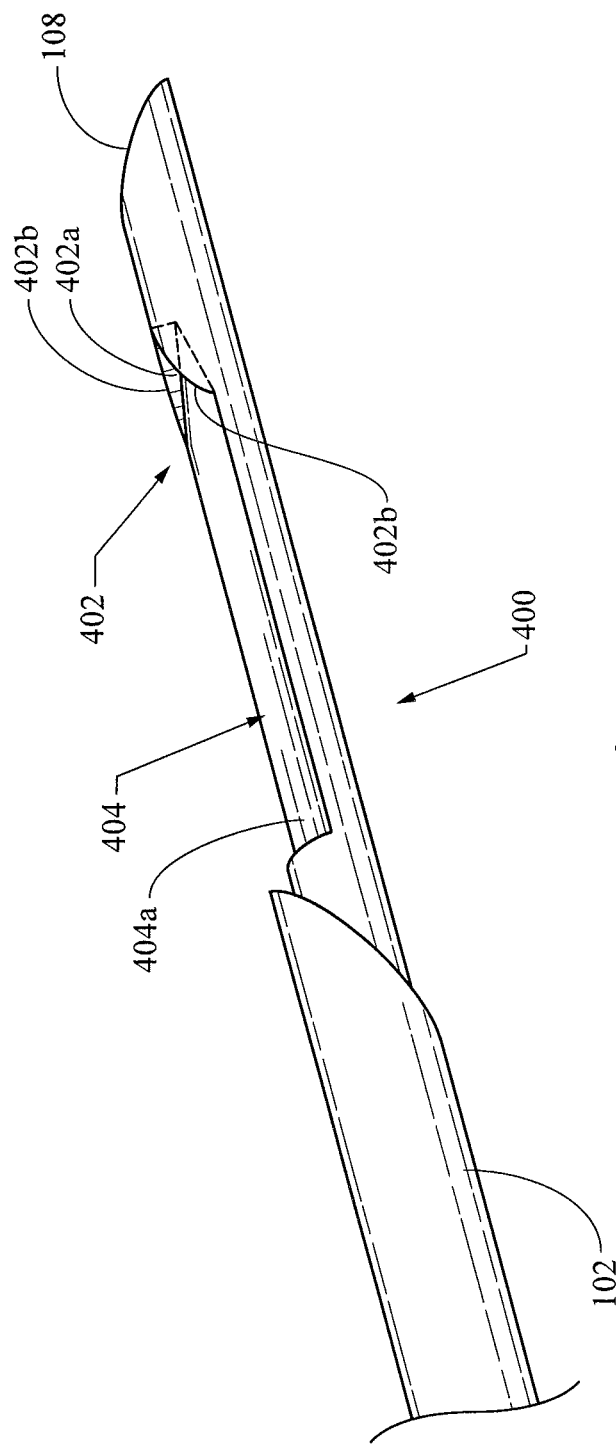
FIG. 4 illustrates a perspective view of an alternate exemplary improved inner mandrel.

The exemplary embodiments illustrated herein provide exemplary apparatuses and methods for maximizing tissue retrieved when using a partial-core biopsy needle. The present invention is not limited to those embodiments described herein, but rather, the disclosure includes all equivalents including those of different shapes, sizes, and configurations including, but not limited to, those used for histological examination of suspected unhealthy pathology including, but not limited to, tumors and cirrhosis. The devices and methods can be used in any field benefiting from a biopsy sample.

A more detailed description of the embodiments will now be given with reference to FIGS. 1A-7. Throughout the disclosure, like reference numerals and letters refer to like elements. The present disclosure is not limited to the embodiments illustrated; to the contrary, the present disclosure specifically contemplates other embodiments not illustrated but intended to be included in the claims.

FIG. 1A illustrates a side view of typical partial-core biopsy needle 100 having proximal portion 100a and distal portion 100b. Inner mandrel 104, having notch 106 and beveled edge 108 is configured for extending out from outer cannula 102 after device 100 is directed to an area for taking a biopsy sample.

FIG. 1B is a cross-sectional view of typical inner mandrel 104 along the line A-A shown in FIG. 1A. Referring to FIGS. 1A and 1B, to form notch 106, void 106a is machine ground into typical inner mandrel 104 such that about one-half is ground out leaving one-half of material 106b remaining thereby forming a half-cylindrical shape.

Again referring to FIGS. 1A and 1B, a user directs device 100 over a target biopsy site wherein inner mandrel 104 is disposed within outer cannula 102 such that notch 106 is within outer cannula 102 and beveled edge 108 extends out from outer cannula 102. Beveled edge 108 provides a cutting surface for penetrating through tissue to reach the targeted tissue. Inner mandrel 104 is then directed out from outer cannula 102 such that notch 106 is exposed. It is desired that void 106a fill with tissue. Outer cannula 102 is then thrown/fired/directed over inner mandrel 104 such that outer cannula 102 may tear a portion of the tissue from its original location leaving the tissue collected in void 106a of notch 106 for later ejection from device 100 and testing.

However, typical partial needle biopsy devices 100, such as that illustrated in FIGS. 1A and 1B, fail to accomplish that which is desired. Namely, the desired volume of targeted tissue is not collected in notch 106 for a variety of reasons.

For example, tissue initially gathered within void 106a of notch 106 is often times not actually captured after outer cannula 102 is thrown over inner mandrel 104. This is because outer cannula 102 pushes tissue out from void 106a of notch 106 as outer cannula 102 closes over notch 106 and inner mandrel 104. The tissue pushed out from void 106a of notch 106 is said to migrate out from notch 106 thereby not being collected for sampling.

Referring to FIG. 1B, another shortcoming of typical partial-core biopsy needle device 100 is, for example, the volume of tissue able to be collected is limited to the size of void 106a of notch 106, and typical inner mandrel 100 has material portion 106b about equal to void 106a. However, merely creating a deeper void 106a to permit a greater volume of tissue to collect within void 106a of notch 106 reduces the stiffness of inner mandrel 104, because the amount of material 106b remaining in notch 106 is thereby reduced, thus increasing the flexibility of inner mandrel 104, especially near the region of notch 106. Even without increasing void 106a of notch 106, current devices suffer from having a flexible inner mandrel 104, especially near the area of notch 106.

The flexibility of inner mandrel 104 is undesired for many reasons. For example, a flexible inner mandrel 104 will deflect from the targeted tissue, especially tissue of a harder composition, thereby missing the target location. Flexible inner mandrel 104 may also cause inner mandrel 104 to bend into other tissue, thereby damaging it or causing trauma to it. The deflection and bending of inner mandrel 104 also slows the firing of outer cannula 102 over inner mandrel 104 because outer cannula 102 is unable to follow a straight pathway along inner mandrel 104. Following the deflected/bent/curved path of inner mandrel 104 may cause outer cannula 102 to pull away from inner mandrel 104 thereby potentially causing inner mandrel 104 to tear away from the tissue in which it is dwelling thereby potentially causing damage and trauma to it and the surrounding area, and it may also collect undesired tissue. Furthermore, the deflection of inner mandrel 104 may cause outer cannula 102 to jam within void 106a of notch 106 of inner mandrel 104 when thrown/fired/advanced over inner mandrel 104 because the pathway of outer cannula 102 is not straight due to the deflection of inner mandrel 104.

It has been discovered that the notch of an inner mandrel can be improved such that tissue migration is reduced. It has also been discovered that a greater volume of tissue can be collected without increasing the flexibility of inner mandrel thereby permitting a larger targeted biopsy sample to be collected with decreased inner mandrel deflection.

FIG. 2 illustrates a side view of an exemplary improved inner mandrel 200. Improved inner mandrel 200 provides for greater tissue retention, whether it be muscle, organ, or any other types of tissue from a body. Body is not limited to a human body; indeed others are contemplated including, but not limited to, animals or any portion thereof. User is not limited to a human being; indeed anything capable of using the device is contemplated including, but not limited to, a machine.

Improved inner mandrel 200 reduces or eliminates tissue migration. Improved mandrel 200 is made from stainless steel, although other materials are contemplated including any other suitable medial grade material including, but not limited to, being made in whole or in part from plastic, Platinum-Iridium alloy, gold, tungsten, echogenic, and other materials that may or may not provide for visualization using a visualization device, including but not limited to fluoroscopy, x-ray, ultrasound, or magnetic resonance imaging (MRI). An echogenic material includes surface irregularities that reflect ultrasonic waves and thus, allows the material to be seen with ultrasonic imaging devices. Echogenic techniques are described in U.S. Pat. Nos. 5,081,997 and 5,289,831 and are hereby incorporated by reference in their entirety.

Improved notch 204 includes edge 202 having a wall surface including vertical portion 202a and angled shoulder 202b, although other configurations are contemplated, including but not limited to, vertical portion 202a, in whole or in part, and angled shoulder 202b, in whole or in part, may have a generally concave surface or a generally convex surface or combination thereof in addition to the generally flat surface illustrated. Vertical portion 202a provides a stop position for tissue as outer cannula 102 is thrown over improved inner mandrel 200. Vertical portion 202a is about one-quarter of the diameter of inner mandrel 200, although other dimensions are contemplated depending upon the tissue to be collected and the needs of the patient. Void 204a, for partially encapsulating tissue, is about half the diameter of inner mandrel 200 and about 1 cm to 2 cm long and is constructed by machine grinding into inner mandrel 200 and is bound by a surface having a longitudinal axis generally parallel to inner mandrel 200 body, although other means for construction are contemplated including, but not limited to, laser cutting. For example, in addition to void 204a being bounded by a generally flat surface, it could also be bound by a generally concave surface or generally convex surface or combination thereof. Other dimensions and configurations are contemplated depending upon the tissue to be collected and the needs of the patient. Indeed, the principles described can be applied in whole or in part to any of the embodiments, including but not limited to, those illustrated in FIGS. 3-7.

Accordingly, as outer cannula 102 is pushed over inner mandrel 200 and notch 204, edge 202 will reduce or eliminate tissue migration out from void 204a of notch 204 because compressed tissue will abut vertical portion 202a thereby reducing or eliminating tissue from migrating out from void 204a of notch 204.

Shoulder 202b provides a deflection point for outer cannula 102, such that outer cannula 102 will not jam into improved notch 204 as it travels over improved inner mandrel 200. Shoulder is about one-quarter the diameter of inner mandrel 200, is set at about a 60-degree angle from the axis of inner mandrel 200 and is machine ground into inner mandrel 200, although other means for construction are contemplated including, but not limited to, laser cutting. Other dimensions and configurations are contemplated depending upon the tissue to be collected and the needs of the patient.

FIG. 3 illustrates a side view of an alternate exemplary improved inner mandrel 300 having beveled edge 108, improved notch 304, and edge 302. Edge 302 includes angled portion 302a, protruding into void 304a, and shoulder 302b.

Angled portion 302a provides a stop position for tissue as outer cannula 102 is thrown over improved inner mandrel 300. Angled portion 302a is about 1 mm long and is set at about a 30-degree angle, although other dimensions and configurations are contemplated depending upon the tissue to be collected and the needs of the patient. Void 304a of improved notch 304 is about one-half the diameter deep of inner mandrel 300 and about 1 cm to 2 cm long and is constructed by machine grinding into inner mandrel 300, although other means for construction are contemplated including, but not limited to, laser cutting. Other dimensions and configurations are contemplated depending upon the tissue to be collected and the needs of the patient.

Accordingly, as outer cannula 102 is pushed over inner mandrel 300 and notch 304, edge 302 will reduce or eliminate tissue migration out from void 304a of notch 304 because compressed tissue will abut into angled portion 302a thereby reducing or eliminating tissue from migrating out from void 304a of notch 304.

Shoulder 302b provides a deflection point for outer cannula 102, such that outer cannula 102 will not jam into improved notch 304 as it travels over improved inner mandrel 300. Shoulder is about 1 mm long, is set at about a 45-degree angle, and is machine ground into inner mandrel 300, although other means for construction are contemplated including, but not limited to, laser cutting. Other dimensions and configurations are contemplated depending upon the tissue to be collected and the needs of the patient.

FIG. 4 illustrates a perspective view of an alternate improved exemplary inner mandrel 400 having beveled edge 108, improved notch 404, and edge 402. Edge 402 includes gathering area 402a and shoulders 402b that project distally to create a depression, although other configurations are contemplated, including but not limited to, projecting proximally.

Gathering area 402a provides a stop position for tissue as outer cannula 102 is thrown over improved inner mandrel 400. Gathering area 402a is about 2 mm long, one-half the diameter deep of inner mandrel 400, and is set at about a 45-degree angle, although other dimensions and configurations are contemplated depending upon the tissue to be collected and the needs of the patient. Void 404a of improved notch 404 is about one-half the diameter deep of inner mandrel 400 and about 1 cm to 2 cm long and is constructed by machine grinding into inner mandrel 400, although other means for construction are contemplated including, but not limited to, laser cutting. Other dimensions and configurations are contemplated depending upon the tissue to be collected and the needs of the patient.

Accordingly, as outer cannula 102 is pushed over inner mandrel 400 and notch 404, edge 402 will reduce or eliminate tissue migration out from void 404a of notch 404 because compressed tissue will gather and abut into gathering area 402a thereby reducing or eliminating tissue from migrating out from void 404a of notch 404.

Shoulders 402b provide a deflection point for outer cannula 102, such that outer cannula 102 will not jam into improved notch 404 as it travels over improved inner mandrel 400. Shoulders are about 2 mm long, are set at about a 45-degree angle, and are machine ground into inner mandrel 400, although other means for construction are contemplated including, but not limited to, laser cutting. Other dimensions and configurations are contemplated depending upon the tissue to be collected and the needs of the patient.

FIG. 5 illustrates a side view of an alternate exemplary inner mandrel 500 having beveled edge 108, improved notch 504, and shoulder 502. Notch 504 includes ridges 504a.

Ridges 504a are tapered, pointed, stepped changes in the outer surface of notch 504 such that they will grip tissue as outer cannula 102 is thrown over improved inner mandrel 500. Ridges 504a are about 2 mm long, about 1 mm deep, and are set at about a 27-degree angle, although other dimensions and configurations are contemplated depending upon the tissue to be collected and the needs of the patient. Likewise, the number of ridges is not limited; more or less ridges are contemplated, including one. It is preferred, although in no way required, that ridges 504a be spaced about 2 mm apart, although other dimensions and configurations are contemplated depending upon the tissue to be collected and the needs of the patient. Void 504b of improved notch 504 is about one-half the diameter of inner mandrel 500 and about 1 cm to 2 cm long including the region with the ridges and is constructed by machine grinding into inner mandrel 500, although other means for construction are contemplated including, but not limited to, laser cutting. Other dimensions and configurations are contemplated depending upon the tissue to be collected and the needs of the patient.

Accordingly, as outer cannula 102 is pushed over inner mandrel 500 and notch 504, ridges 504a will reduce or eliminate tissue migration out from void 504b of notch 504 because compressed tissue will frictionally adhere to ridges 504a thereby reducing or eliminating tissue from migrating out from void 504b of notch 504. It is contemplated that other features may be added to the surface of notch 504 along its length thereby reducing or eliminating movement of tissue.

Shoulder 502 provides a deflection point for outer cannula 102, such that outer cannula 102 will not jam into improved notch 504 as it travels over improved inner mandrel 500. Shoulder is about 2 mm long, is set at about a 45-degree angle, and is machine ground into inner mandrel 500, although other means for construction are contemplated including, but not limited to, laser cutting. The angle of the proximal portion of each ridge 504a may be 90-degrees from the axis of inner mandrel 500 or may be angled backwards to have an overhang like a saw blade. Other dimensions and configurations are contemplated depending upon the tissue to be collected and the needs of the patient.

Referring again to FIGS. 1A and 1B, typical inner mandrel 104 has about roughly a semicircular cross-section at notch 106, along the line A-A, wherein void 106a is machine ground into inner mandrel 104 such that only one-half of the original typical inner mandrel 104 material 106b remains, thus forming notch 106. Thus, the maximum size of the sample is limited by the volume of void 106a of notch 106. But if void 106a into inner mandrel 104 were cut deeper creating a bigger void 106a, inner mandrel 104 may further deflect upon reaching hard tissue and reduce even more the target accuracy and volume of tissue collected.

It has been discovered that the cross-section of inner mandrel to form a void for additional tissue volume may be configured in such a manner as to increase the volume of space for tissue collection without reducing the rigidity of inner mandrel. Specifically, the cross-section may be configured to locate material as far from the neutral axis of bending. The flexural rigidity of about roughly a semicircular inner mandrel will be less in the Y-axis than the Z-axis, therefore moving material to the top and bottom even at the expense of removing it from the side will result in a decreased total deflection. This can be seen from the equation of the moment of inertia of a beam: $I=\int_A y^2 \, dA$, wherein "dA" is an elemental area, and "y" is the perpendicular distance to the element "dA" from the X-axis.

For example, FIG. 6 illustrates a cross-sectional view of an exemplary notch 600 of an exemplary inner mandrel that resists flexing and deflection, even at notch 600 while at the same time permitting a greater volume of tissue to be collected as compared with typical notch 106 depicted in FIGS. 1A and 1B.

Referring again to FIG. 6, to form notch 600, void 604 is machine ground (other means for construction are contemplated including, but not limited to, laser cutting) into about roughly an elongated tubular inner mandrel such that void 604 represents about 60% of the cross-sectional area of notch 600, and material 602 represents about 40% of the cross-sectional area of notch 600. Material 602 about roughly comprises a shape, shown in cross-section, of a surface of a sector, but the vertex is located in the interior of the circle on the opposite side of the diameter of the circle. More specifically, about roughly, material 602, shown in cross-section, is about roughly the union of a segment of a circle S and adjacent triangle T, abutting segment S and formed within the circle, wherein triangle T has one side as chord, illustrated with dashed-line C-C, forming segment S. Vertex V of triangle T is located in the interior of the circle and about one-sixth of the total diameter above the centerline on the opposite side of diameter, illustrated with dashed-line D-D, which is about roughly parallel to chord C-C.

Material 602 allows a similar rigidity to be achieved in the Y-axis while using less material, thereby allowing for a larger void 604 such that the volume of space for tissue collection is increased. Other dimensions and configurations of void 604, material 602, and vertex V of material 602 are contemplated depending upon the tissue to be collected and the needs of the patient, including but not limited to, having void project downward into material.

FIG. 7 illustrates a cross-sectional view of an alternate exemplary notch 700 of an exemplary inner mandrel that resists flexing and deflection, even at notch 700 while at the same time permitting a greater volume of tissue to be collected as compared with typical notch 106 depicted in FIGS. 1A and 1B.

Referring again to FIG. 7, to form notch 700, void 704 is laser cut (other means for construction are contemplated including, but not limited to, machine grounding) into about roughly an elongated tubular inner mandrel such that void 704 represents about 80% of the cross-sectional area of notch 700, and total material 702 represents about 20% of the cross-sectional area of inner mandrel, wherein material 702 is about equally distributed against sides, such that each portion of surface of material 702 illustrated in cross-section is about roughly a circular segment having a chord of about 0.727 times the diameter long, although it is contemplated that each cord can be of varying lengths such that material 702 is or is not equally distributed. Accordingly void forms a hole. Other dimensions and configurations of void 704 and material 702 are contemplated depending upon the tissue to be collected and the needs of the patient.

As can be seen in FIGS. 6 and 7, the inner mandrel has a generally circular cross-sectional area having four equally sized and shaped quadrants, and void 604, 704 of notch 600, 700 is bounded by surface material 602, 702 such that material 602, 702 is less than one-half the total cross-sectional area of the inner mandrel and is disposed into each of the four quadrants.

Use of the methods and devices for reducing inner mandrel deflection and increasing the volume of space available for tissue collection may be used in conjunction with or alone from the methods and devices for reducing tissue migration, and visa versa.

From the foregoing, it can be seen that migration of tissue from an inner mandrel can be reduced, the volume of space available for tissue collection can be increased, and inner mandrel flexibility and deflection can be decreased.

What is claimed is:

1. A biopsy device comprising:
   a first elongated tubular body extending along a central longitudinal axis and having a proximal portion and a distal portion;
   a second elongated tubular body having a proximal portion and a distal portion, the distal portion having an angled distal end that is movably disposed over the first elongated tubular body; and
   a notch disposed into the distal portion of the first elongated tubular body, wherein the notch comprises:
     a void configured for partially encapsulating a tissue;
     a surface disposed in communication with the void, wherein the surface defines a horizontal boundary of at least a portion of the void, wherein the surface extends distally to and terminates at a distal edge, and wherein the surface is generally parallel to the central longitudinal axis of the first elongated tubular body;
     a tissue stop in communication with a distal portion of the void and configured for preventing tissue migration, the tissue stop extending between an inner edge and an outer edge, the inner edge directly connected to the distal edge of the surface; and
     a shoulder extending between an inner proximal edge and an outer distal edge, the inner proximal edge being in communication with and directly connected to the outer edge of the tissue stop, the shoulder being disposed at an angle that is oriented in an outwardly distal direction relative to the central longitudinal axis of the first elongated tubular body such that the inner proximal edge is disposed proximal of the outer distal edge, and such that the inner proximal edge is disposed closer to the central longitudinal axis than the outer distal edge, the angle being different from the surface and configured for deflecting the second elongated tubular body when directed distally over the notch, the shoulder being spaced apart from the surface, the outer distal edge directly connected to an outer surface of the first elongated tubular body, wherein the outer distal edge is directly connected to the outer surface of the elongated tubular body at a location distal to the distal edge of the surface, and wherein the outer distal edge of the tissue stop is disposed distally of a distal most end of the notch,
   wherein the tissue stop consists of a unitary vertical surface extending between the inner edge and the outer edge, and that is perpendicular to the central longitudinal axis of the first elongated tubular body, wherein the unitary vertical surface is disposed proximally of the shoulder, wherein the unitary vertical surface is disposed between and directly connected to and between the inner proximal edge of the shoulder and the distal edge of the surface of the notch, wherein the surface of the notch does not extend distally beyond either the unitary vertical surface or the shoulder, wherein the unitary vertical surface and the shoulder together fully define a distal most boundary of the void, and wherein the notch does not comprise a void area that is coincident to the surface and distal to the unitary vertical surface.

2. The biopsy device of claim 1, wherein the tissue stop further comprises an angled surface protruding into a distal end of the void.

3. The biopsy device of claim 1, wherein the tissue stop further comprises a gathering area, wherein the shoulder further comprises two shoulders, and wherein the two shoulders are configured as a distal boundary of the gathering area.

4. The biopsy device of claim 1, wherein the tissue stop further comprises at least one ridge disposed within the surface of the notch.

5. The biopsy device of claim 1, wherein the first elongated tubular body further comprises a cutting edge disposed at the distal portion of the first elongated tubular body.

6. The biopsy device of claim 1, wherein the void represents about 60-80% of a cross-sectional area of the notch.

7. The biopsy device of claim 1, wherein a cross-section of the surface of the notch further comprises a union of a segment of a circle and an adjacent triangle, wherein the triangle abuts the segment and is formed within the circle, wherein the triangle has one side as a chord of the circle thereby forming the segment, and wherein a vertex of the triangle is located in an interior of the circle and about one-sixth of a diameter on an opposite side of the diameter of the circle, wherein the diameter is about parallel to the chord.

8. The biopsy device of claim 1, wherein a cross-section of the surface of the notch further comprises about a sector-shape.

9. The biopsy device of claim 1, wherein the surface of the notch further comprises two surfaces, wherein each surface has a cross-sectional shape of a semicircle, and wherein the two surfaces are configured to form at least two side outer boundaries of the void such that the void is a hole through the elongated tubular body.

10. A biopsy device comprising:
an elongated tubular body having a proximal portion and a distal portion; and
a notch disposed into the distal portion of the elongated tubular body, wherein the notch comprises:
a void configured for partially encapsulating a tissue;
a surface disposed in communication with the void, wherein the surface defines a horizontal boundary of at least a portion of the void, wherein the surface extends distally to and terminates at a distal most edge, wherein the surface and the void are configured to reduce the flexibility of the elongated tubular body;
a tissue stop in communication with a distal portion of the void and configured for preventing tissue migration, the tissue stop consisting of a unitary vertical surface disposed at a distal end of the void and directly connected to the distal most edge of the surface of the void; and
a shoulder in communication with the tissue stop disposed at an angle that is oriented in an outwardly distal direction, the angle being different from the surface and configured for deflecting a second elongated tubular body when directed distally over the notch, the shoulder extending between and inner proximal edge and an outer distal edge, the inner proximal edge connected to the tissue stop, the outer distal edge connected to an outer surface of the elongated tubular body, the outer edge being disposed distally of the inner edge, the shoulder being spaced apart from the surface, wherein the angle of the shoulder intersects the surface of the void at a location proximal of the unitary vertical surface, and wherein the outer distal edge of the shoulder is disposed distally of the distal end of the void,
wherein the unitary vertical surface of the tissue stop is disposed between and directly connected to both the shoulder and the distal most edge of the surface of the notch, wherein the unitary vertical surface is disposed proximally of the shoulder, wherein the unitary vertical surface is disposed distally of the distal most edge of the surface of the notch, wherein the surface does not extend distally beyond either the unitary vertical surface or the shoulder, and wherein the notch does not comprise a void area that is coincident to the surface and distal to the unitary vertical surface.

11. The biopsy device of claim 10, wherein the void represents 60-80% of a cross-sectional area of the notch.

12. The biopsy device of claim 10, wherein a cross-section of the surface of the notch further comprises a union of a segment of a circle and an adjacent triangle, wherein the triangle abuts the segment and is formed within the circle, wherein the triangle has one side as a chord of the circle thereby forming the segment, and wherein a vertex of the triangle is located in an interior of the circle and on an opposite side of a diameter of the circle, wherein the diameter is parallel to the chord.

13. The biopsy device of claim 10, wherein a cross-section of the surface of the notch further comprises about a sector-shape.

14. The biopsy device of claim 10, wherein the surface of the notch further comprises two surfaces, wherein each surface has a cross-sectional shape of a semicircle, and wherein the two surfaces are configured to form at least two outer boundaries of the void such that the void is a hole through the elongated tubular body.

15. The biopsy device of claim 10, wherein the tissue stop further comprises a gathering area, wherein the shoulder further comprises two shoulders, and wherein the two shoulders are configured as a distal boundary for the gathering area.

16. A partial-core biopsy device comprising;
an elongated tubular body having a proximal portion, a distal portion, and a generally circular cross-sectional area having four equally sized and shaped quadrants; and
a notch disposed into the distal portion of the elongated tubular body, wherein the notch comprises a void that is bounded by a surface, the void configured for partially encapsulating a tissue, wherein the notch comprises a means for reducing tissue migration, and wherein a cross-sectional area of the void is less than one-half the total cross-sectional area of the elongated tubular body and the surface is disposed within each of the four quadrants,
wherein the means for reducing tissue migration comprises a tissue stop having a unitary vertical surface disposed at a distal end of the notch, the unitary vertical surface having an inner edge that is adjacent to and connected directly with a distal-most edge of the distal end of the notch, wherein the tissue stop further comprises a shoulder in communication with the tissue stop and disposed at an angle that is oriented in an outwardly distal direction relative to a central longitudinal axis of the elongated tubular body, the angle being different from both the unitary vertical surface and the surface of the notch, the shoulder being spaced apart from the surface and configured for deflecting a second elongated tubular body when directed distally over the notch, wherein the shoulder comprises an outer distal edge that intersects an outer surface of the elongated tubular body at a location distal of both the unitary vertical surface and the surface of the notch, the outer distal edge being disposed distally of the distal-most edge of the distal end of the notch, wherein the vertical unitary surface is disposed proximally of the shoulder, wherein the unitary vertical surface is disposed between and directly connected to both the shoulder and the distal-most edge of the surface of the notch, wherein the surface of the notch does not extend distally beyond either the unitary vertical surface or the shoulder, and wherein the notch does not comprise a void area that is coincident to the surface and distal to the unitary vertical surface.

17. The biopsy device of claim 16, wherein the surface of the notch further comprises a pair of planar surfaces that are connected to each other along an inner edge that is parallel to a longitudinal axis of the elongated tubular body, the pair of planar surfaces being disposed at an angle to each other, each planar surface having an outer edge that is directly connected to an outer surface of the elongate tubular body.

18. The biopsy device of claim 17, wherein the inner edges of the pair of planar surface intersect with each other to form an angled vertex.

19. The biopsy device of claim 16, wherein the surface of the notch defines a cross-sectional area of material opposing said void, said cross-sectional area of the material comprising a segment of a circular and an adjacent triangle.

* * * * *